United States Patent [19]

Savino et al.

[11] Patent Number: 5,789,552

[45] Date of Patent: Aug. 4, 1998

[54] INTERLEUKIN-6 RECEPTOR ANTAGONISTS

[75] Inventors: Rocco Savino, Pomezia; Armin Lahm, Rome; Gennaro Cillberto, Casalpalocco, all of Italy

[73] Assignee: Istituto di Ricerche di Biologica Molecolare P. Angeletti S.p.A., Pomezia, Italy

[21] Appl. No.: 567,047

[22] Filed: Dec. 4, 1995

Related U.S. Application Data

[62] Division of Ser. No. 387,924, Feb. 23, 1995.

[30] Foreign Application Priority Data

Jun. 23, 1993 [IT] Italy ................... RM93A0409

[51] Int. Cl.$^6$ ............ C07K 14/54; C12N 15/24; C12N 15/63; C12N 5/10
[52] U.S. Cl. ............ 530/351; 435/69.52; 435/325; 435/252.3; 435/320.1; 930/140
[58] Field of Search ................... 435/7.1, 7.21, 435/69.52; 530/351; 930/141

[56] References Cited

U.S. PATENT DOCUMENTS

| | | | |
|---|---|---|---|
| 5,132,403 | 7/1992 | Kishimoto | 530/351 |
| 5,210,075 | 5/1993 | Scholz et al. | 514/14 |
| 5,506,107 | 4/1996 | Cunningham et al. | 435/7.21 |

OTHER PUBLICATIONS

Rudinger, J. 1976. Characteristics of the amino acids as components of apeptide hormone sequence. In: Parsons JA, ed. Peptide hormones. Baltimore, Univ Park Press. pp. 1–7, 1976.

*Primary Examiner*—John Ulm
*Assistant Examiner*—Christine Saoud
*Attorney, Agent, or Firm*—Browdy and Neimark

[57] ABSTRACT

Disclosed are interleukin-6 receptor antagonists. These receptor antagonists are generated by mutating amino acid positions 31, 35, 118, 121, 175, 176 and/or 183 of human interleukin-6.

6 Claims, 2 Drawing Sheets

SEQUENCE LISTING ( 1 ) GENERAL INFORMATION:

( i i i ) NUMBER OF SEQUENCES: 15

( 2 ) INFORMATION FOR SEQ ID NO: 1:

( i ) SEQUENCE CHARACTERISTICS:
        ( A ) LENGTH: 555 base pairs
        ( B ) TYPE: nucleic acid
        ( C ) STRANDEDNESS: double
        ( D ) TOPOLOGY: linear ( i i ) MOLECULE TYPE: cDNA
        iii) HYPOTHETICAL: no ( i v ) ANTI-SENSE: no ( v ) FRAGMENT TYPE: internal ( v i i ) IMMEDIATE SOURCE:
        ( A ) LIBRARY: production in bacteria ( i x ) FEATURE:
        ( A ) NAME/KEY: IL-6 cDNA
        ( C ) IDENTIFICATION METHOD: polyacrylamide gel ( i x ) FEATURE:
        ( A ) NAME/KEY: CDS
        ( B ) LOCATION: 1..552

( x i ) SEQUENCE DESCRIPTION: SEQ ID NO:1:

```
CCA GTA CCC CCA GGA GAA GAT TCC AAA GAT GTA GCC GCC CCA CAC AGA        48
Pro Val Pro Pro Gly Glu Asp Ser Lys Asp Val Ala Ala Pro His Arg
 1               5                  10                  15

CAG CCA CTC ACG AGC TCA GAA CGA ATT GAC AAA CAA ATT CGG TAC ATC        96
Gln Pro Leu Thr Ser Ser Glu Arg Ile Asp Lys Gln Ile Arg Tyr Ile
             20                  25                  30

CTC GAC GGC ATC TCA GCC TTA AGA AAG GAG ACA TGT AAC AAG AGT AAC       144
Leu Asp Gly Ile Ser Ala Leu Arg Lys Glu Thr Cys Asn Lys Ser Asn
```

|  |  |  |  |  | 35 |  |  |  |  | 40 |  |  |  |  | 45 |  |  |  |
|---|---|---|---|---|---|---|---|---|---|---|---|---|---|---|---|---|---|---|
| ATG | TGT | GAA | AGC | AGC | AAA | GAG | GCA | CTG | GCA | GAA | AAC | AAC | CTG | AAC | CTT | | | 192 |
| Met | Cys | Glu | Ser | Ser | Lys | Glu | Ala | Leu | Ala | Glu | Asn | Asn | Leu | Asn | Leu | | | |
| | 50 | | | | 55 | | | | | 60 | | | | | | | | |
| CCA | AAG | ATG | GCT | GAA | AAA | GAT | GGA | TGC | TTC | CAA | TCT | GGA | TTC | AAT | GAG | | | 240 |
| Pro | Lys | Met | Ala | Glu | Lys | Asp | Gly | Cys | Phe | Gln | Ser | Gly | Phe | Asn | Glu | | | |
| 65 | | | | | 70 | | | | 75 | | | | | | 80 | | | |
| GAG | ACT | TGC | CTG | GTG | AAA | ATC | ATC | ACT | GGT | CTT | TTG | GAG | TTT | GAG | GTA | | | 288 |
| Glu | Thr | Cys | Leu | Val | Lys | Ile | Ile | Thr | Gly | Leu | Leu | Glu | Phe | Glu | Val | | | |
| | | | | 85 | | | | | 90 | | | | | | 95 | | | |
| TAC | CTA | GAG | TAC | CTC | CAG | AAC | AGA | TTT | GAG | AGT | AGT | GAG | GAA | CAA | GCC | | | 336 |
| Tyr | Leu | Glu | Tyr | Leu | Gln | Asn | Arg | Phe | Glu | Ser | Ser | Glu | Glu | Gln | Ala | | | |
| | | | 100 | | | | | 105 | | | | | 110 | | | | | |
| AGA | GCT | GTC | CAG | ATG | AGT | ACA | AAA | GTC | CTG | ATC | CAG | TTC | CTG | CAG | AAA | | | 384 |
| Arg | Ala | Val | Gln | Met | Ser | Thr | Lys | Val | Leu | Ile | Gln | Phe | Leu | Gln | Lys | | | |
| | | 115 | | | | | 120 | | | | | 125 | | | | | | |
| AAG | GCA | AAG | AAT | CTA | GAT | GCA | ATA | ACC | ACC | CCT | GAC | CCA | ACC | ACA | AAT | | | 432 |
| Lys | Ala | Lys | Asn | Leu | Asp | Ala | Ile | Thr | Thr | Pro | Asp | Pro | Thr | Thr | Asn | | | |
| | 130 | | | | | 135 | | | | | 140 | | | | | | | |
| GCC | AGC | CTG | CTG | ACG | AAG | CTG | CAG | GCA | CAG | AAC | CAG | TGG | CTG | CAG | GAC | | | 480 |
| Ala | Ser | Leu | Leu | Thr | Lys | Leu | Gln | Ala | Gln | Asn | Gln | Trp | Leu | Gln | Asp | | | |
| 145 | | | | | 150 | | | | | 155 | | | | | 160 | | | |
| ATG | ACA | ACT | CAT | CTC | ATT | CTG | AGA | TCT | TTT | AAG | GAG | TTC | CTG | CAG | TCC | | | 528 |
| Met | Thr | Thr | His | Leu | Ile | Leu | Arg | Ser | Phe | Lys | Glu | Phe | Leu | Gln | Ser | | | |
| | | | | 165 | | | | | 170 | | | | | 175 | | | | |
| AGC | CTG | AGG | GCT | CTT | CGG | CAA | ATG | TAG | | | | | | | | | | 555 |
| Ser | Leu | Arg | Ala | Leu | Arg | Gln | Met | | | | | | | | | | | |
| | | | 180 | | | | | | | | | | | | | | | |

( 2 ) INFORMATION FOR SEQ ID NO:2:

( i ) SEQUENCE CHARACTERISTICS:
        ( A ) LENGTH: 184 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Pro | Val | Pro | Pro | Gly | Glu | Asp | Ser | Lys | Asp | Val | Ala | Ala | Pro | His | Arg |
|---|---|---|---|---|---|---|---|---|---|---|---|---|---|---|---|
| 1 | | | | 5 | | | | | 10 | | | | | 15 | |

| Gln | Pro | Leu | Thr | Ser | Ser | Glu | Arg | Ile | Asp | Lys | Gln | Ile | Arg | Tyr | Ile |
|---|---|---|---|---|---|---|---|---|---|---|---|---|---|---|---|
| | | | 20 | | | | | 25 | | | | | 30 | | |

| Leu | Asp | Gly | Ile | Ser | Ala | Leu | Arg | Lys | Glu | Thr | Cys | Asn | Lys | Ser | Asn |
|---|---|---|---|---|---|---|---|---|---|---|---|---|---|---|---|
| | | | 35 | | | | 40 | | | | | 45 | | | |

| Met | Cys | Glu | Ser | Ser | Lys | Glu | Ala | Leu | Ala | Glu | Asn | Asn | Leu | Asn | Leu |
|---|---|---|---|---|---|---|---|---|---|---|---|---|---|---|---|
| | 50 | | | | 55 | | | | | 60 | | | | | |

| Pro | Lys | Met | Ala | Glu | Lys | Asp | Gly | Cys | Phe | Gln | Ser | Gly | Phe | Asn | Glu |
|---|---|---|---|---|---|---|---|---|---|---|---|---|---|---|---|
| 65 | | | | | 70 | | | | 75 | | | | | | 80 |

| Glu | Thr | Cys | Leu | Val | Lys | Ile | Ile | Thr | Gly | Leu | Leu | Glu | Phe | Glu | Val |
|---|---|---|---|---|---|---|---|---|---|---|---|---|---|---|---|
| | | | | 85 | | | | | 90 | | | | | | 95 |

| Tyr | Leu | Glu | Tyr | Leu | Gln | Asn | Arg | Phe | Glu | Ser | Ser | Glu | Glu | Gln | Ala |
|---|---|---|---|---|---|---|---|---|---|---|---|---|---|---|---|
| | | | 100 | | | | | 105 | | | | | 110 | | |

| Arg | Ala | Val | Gln | Met | Ser | Thr | Lys | Val | Leu | Ile | Gln | Phe | Leu | Gln | Lys |
|---|---|---|---|---|---|---|---|---|---|---|---|---|---|---|---|
| | | 115 | | | | | 120 | | | | | 125 | | | |

| Lys | Ala | Lys | Asn | Leu | Asp | Ala | Ile | Thr | Thr | Pro | Asp | Pro | Thr | Thr | Asn |
|---|---|---|---|---|---|---|---|---|---|---|---|---|---|---|---|
| | 130 | | | | | 135 | | | | | 140 | | | | |

| Ala | Ser | Leu | Leu | Thr | Lys | Leu | Gln | Ala | Gln | Asn | Gln | Trp | Leu | Gln | Asp |
|---|---|---|---|---|---|---|---|---|---|---|---|---|---|---|---|
| 145 | | | | | 150 | | | | | 155 | | | | | 160 |

| Met | Thr | Thr | His | Leu | Ile | Leu | Arg | Ser | Phe | Lys | Glu | Phe | Leu | Gln | Ser |
| | | | | 165 | | | | | 170 | | | | | 175 | |

| Ser | Leu | Arg | Ala | Leu | Arg | Gln | Met |
| | | | | 180 | | | |

( 2 ) INFORMATION FOR SEQ ID NO:3:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: synthetic DNA ( i i i ) HYPOTHETICAL: no ( i v ) ANTI-SENSE: no ( v ) FRAGMENT TYPE: internal ( v i i ) IMMEDIATE SOURCE:
        ( A ) LIBRARY: oligonucleotide synthesizer ( i x ) FEATURE:
        ( A ) NAME/KEY: IL-6 31D35 PCR
        ( C ) IDENTIFICATION METHOD: polyacrylamide gel ( x i ) SEQUENCE DESCRIPTION: SEQ ID NO:3:

```
CGCACGAGCT CAGAACGAAT TGACAAACAA ATTCGGKACA TCCTCGACYD TATCTCAGCC      60

TTAAGAAAGG                                                             70
```

( 2 ) INFORMATION FOR SEQ ID NO:4:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: synthetic DNA ( i i i ) HYPOTHETICAL: no ( i v ) ANTI-SENSE: yes ( v ) FRAGMENT TYPE: internal ( v i i ) IMMEDIATE SOURCE:
        ( A ) LIBRARY: oligonucleotidic synthetizer ( i x ) FEATURE:
        ( A ) NAME/KEY: IL-6 118RCLF/121VD
        ( C ) IDENTIFICATION METHOD: polyacrylamide gel ( x i ) SEQUENCE DESCRIPTION: SEQ ID NO:4:

```
CGCATCTAGA TTCTTTGCCT TTTTCTGCAG GAACTGGATC AGGWCTTTTG TGMRCATCTG      60

CACAGCTCTG GC                                                          72
```

( 2 ) INFORMATION FOR SEQ ID NO:5:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: synthetic DNA ( i i i ) HYPOTHETICAL: no ( i v ) ANTI-SENSE: yes ( v ) FRAGMENT TYPE: carboxi-terminal ( v i i ) IMMEDIATE SOURCE:
    ( A ) LIBRARY: oligonucleotide synthesizer ( i x ) FEATURE:
    ( A ) NAME/KEY: IL-6 QSLQ (AS)
    ( C ) IDENTIFICATION METHOD: polyacrylamide gel ( x i ) SEQUENCE DESCRIPTION: SEQ ID NO:5:

```
CCGGGCGGCC GCCCTACATM NNCCGMNNAG CCCTCAGMNN GGAMNNCAGG AACTCCTTAA    60
AG                                                                   62
```

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: synthetic DNA ( i i i ) HYPOTHETICAL: no ( i v ) ANTI-SENSE: no ( v ) FRAGMENT TYPE: internal ( v i i ) IMMEDIATE SOURCE:
        ( A ) LIBRARY: oligonucleotide synthesizer ( i x ) FEATURE:
        ( A ) NAME/KEY: IL-6 QSLQ pr. Bam
        ( C ) IDENTIFICATION METHOD: polyacrylamide gel ( x i ) SEQUENCE DESCRIPTION: SEQ ID NO:6:

```
CGCGGATCCT TTAAGGAGTT CCTG                                           24
```

( 2 ) INFORMATION FOR SEQ ID NO:7:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: synthetic DNA ( i i i ) HYPOTHETICAL: no ( i v ) ANTI-SENSE: no ( v ) FRAGMENT TYPE: carboxi-terminal ( v i i ) IMMEDIATE SOURCE:
        ( A ) LIBRARY: oligonucleotide synthesizer ( i x ) FEATURE:
        ( A ) NAME/KEY: 175I/167R/183A (S)
        ( C ) IDENTIFICATION METHOD: polyacrylamide gel ( x i ) SEQUENCE DESCRIPTION: SEQ ID NO:7:

```
GCCTGAGATC TTTTAAGGAG TTCCTGATCC GTAGCCTGAG GGCTCTTCGG GCTATGTAGG    60
GCGGCCGCAT GGC                                                       73
```

( 2 ) INFORMATION FOR SEQ ID NO:8:

( i ) SEQUENCE CHARACTERISTICS:
        ( A ) LENGTH: 73 base pairs
        ( B ) TYPE: nucleic acid ( C ) STRANDEDNESS: single stranded
                    ( D ) TOPOLOGY: linear ( i i ) MOLECULE TYPE: synthetic DNA ( i i i ) HYPOTHETICAL: no ( i v ) ANTI-SENSE: yes ( v ) FRAGMENT TYPE: internal ( v i i ) IMMEDIATE SOURCE:
                    ( A ) LIBRARY: oligonucleotide synthesizer ( i x ) FEATURE:
                    ( A ) NAME/KEY: 175I/167R/183A (AS)
                    ( C ) IDENTIFICATION METHOD: polyacrylamide gel ( x i ) SEQUENCE DESCRIPTION: SEQ ID NO:8:

GCCATGCGGC CGCCCTACAT AGCCCGAAGA GCCCTCAGGC TACGGATCAG GAACTCCTTA          60

AAAGATCTCA GGC          73

( 2 ) INFORMATION FOR SEQ ID NO:9:

( i ) SEQUENCE CHARACTERISTICS:
                    ( A ) LENGTH: 16 amino acids
                    ( B ) TYPE: amino acid
                    ( D ) TOPOLOGY: linear ( i i ) MOLECULE TYPE: protein ( i i i ) HYPOTHETICAL: no ( v ) FRAGMENT TYPE: internal ( v i i ) IMMEDIATE SOURCE:
                    ( A ) LIBRARY: production in bacteria as recombinant protein ( i x ) FEATURE:
                    ( A ) NAME/KEY: wild type interleukin- 6
                    ( C ) IDENTIFICATION METHOD: polyacrylamide gel
                    ( D ) OTHER INFORMATION: sequence of wild type of interleukin 6,
                        from position 27 to position 42

( x i ) SEQUENCE DESCRIPTION: SEQ ID NO:9:

Lys Gln Ile Arg Tyr Ile Leu Asp Gly Ile Ser Ala Leu Arg Lys Glu
 1               5                  10                  15

( 2 ) INFORMATION FOR SEQ ID NO:10:

( i ) SEQUENCE CHARACTERISTICS:
                    ( A ) LENGTH: 16 amino acids
                    ( B ) TYPE: amino acid
                    ( D ) TOPOLOGY: linear ( i i ) MOLECULE TYPE: protein ( i i i ) HYPOTHETICAL: no ( v ) FRAGMENT TYPE: internal ( v i i ) IMMEDIATE SOURCE:
                    ( A ) LIBRARY: production in bacteria as recombinant protein ( i x ) FEATURE:
                    ( A ) NAME/KEY: Lys27Ala, Gly35Gln, Ile36Thr
                    ( C ) IDENTIFICATION METHOD: polyacrylamide gel
                    ( D ) OTHER INFORMATION: sequence of a mutant form of interleuki
                        6, from position 27 to position 42

( x i ) SEQUENCE DESCRIPTION: SEQ ID NO:10:

Ala Gln Ile Arg Tyr Ile Leu Asp Gln Thr Ser Ala Leu Arg Lys Glu
 1               5                  10                  15

( 2 ) INFORMATION FOR SEQ ID NO:11:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( i i i ) HYPOTHETICAL: no ( v ) FRAGMENT TYPE: internal ( v i i ) IMMEDIATE SOURCE:
        ( A ) LIBRARY: production in bacteria as recombinant protein ( i x ) FEATURE:
        ( A ) NAME/KEY: Tyr31Asp, Gly35Phe
        ( C ) IDENTIFICATION METHOD: polyacrylamide gel
        ( D ) OTHER INFORMATION: sequence of a mutant form of interleuki
            6, from position 27 to position 42

( x i ) SEQUENCE DESCRIPTION: SEQ ID NO:11:

```
Lys Gln Ile Arg Asp Ile Leu Asp Tyr Ile Ser Ala Leu Arg Lys Glu
 1               5                  10                  15
```

( 2 ) INFORMATION FOR SEQ ID NO:12:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( i i i ) HYPOTHETICAL: no ( v ) FRAGMENT TYPE: internal ( v i i ) IMMEDIATE SOURCE:
        ( A ) LIBRARY: production in bacteria as recombinant protein ( i x ) FEATURE:
        ( A ) NAME/KEY: Tyr31Asp, Gly35Phe
        ( C ) IDENTIFICATION METHOD: polyacrylamide gel
        ( D ) OTHER INFORMATION: sequence of a mutant form of
            interleukin 6, from position 27 to position 42

( x i ) SEQUENCE DESCRIPTION: SEQ ID NO:12:

```
Lys Gln Ile Arg Asp Ile Leu Asp Phe Ile Ser Ala Leu Arg Lys Glu
 1               5                  10                  15
```

( 2 ) INFORMATION FOR SEQ ID NO:13:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( i i i ) HYPOTHETICAL: no ( v ) FRAGMENT TYPE: internal ( v i i ) IMMEDIATE SOURCE:
        ( A ) LIBRARY: production in bacteria as recombinant protein ( i x ) FEATURE:
        ( A ) NAME/KEY: Tyr31Asp, Gly35Leu, Glu42Ala
        ( C ) IDENTIFICATION METHOD: polyacrylamide gel
        ( D ) OTHER INFORMATION: sequence of a mutant form
            of interleukin 6, from position 27 to position 42

( x i ) SEQUENCE DESCRIPTION: SEQ ID NO:13:

```
Lys Gln Ile Arg Asp Ile Leu Asp Leu Ile Ser Ala Leu Arg Lys Ala
 1               5                    10                  15
```

( 2 ) INFORMATION FOR SEQ ID NO:14:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( i i i ) HYPOTHETICAL: no ( v ) FRAGMENT TYPE: internal ( v i i ) IMMEDIATE SOURCE:
        ( A ) LIBRARY: production in bacteria as recombinant protein ( i x ) FEATURE:
        ( A ) NAME/KEY: Tyr31Asp, Gly35His
        ( C ) IDENTIFICATION METHOD: polyacrylamide gel
        ( D ) OTHER INFORMATION: sequence of a mutant form of
            interleukin 6, from position 27 to position 42

( x i ) SEQUENCE DESCRIPTION: SEQ ID NO:14:

```
Lys Gln Ile Arg Asp Ile Leu Asp His Ile Ser Ala Leu Arg Lys Glu
 1               5                    10                  15
```

( 2 ) INFORMATION FOR SEQ ID NO:15:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( i i i ) HYPOTHETICAL: no ( v ) FRAGMENT TYPE: internal ( v i i ) IMMEDIATE SOURCE:
        ( A ) LIBRARY: production in bacteria as recombinant protein ( i x ) FEATURE:
        ( A ) NAME/KEY: Tyr31Asp, Gly35Cys
        ( C ) IDENTIFICATION METHOD: polyacrylamide gel
        ( D ) OTHER INFORMATION: sequence of a mutant form of
            interleukin 6, from position 27 to position42

( x i ) SEQUENCE DESCRIPTION: SEQ ID NO:15:

```
Lys Gln Ile Arg Asp Ile Leu Asp Cys Ile Ser Ala Leu Arg Lys Glu
 1               5                    10                  15
```

INTERLEUKIN-6 RECEPTOR ANTAGONISTS

This is a division of parent application Ser. No. 08/387,924, filed Feb. 23, 1995, now abandoned, which is the national stage application of PCT/IT94/00095, filed Jun. 23, 1994.

DESCRIPTION

The present invention relates to a methodology for selecting superagonists, antagonists and superantagonists of hormones whose receptor complex includes gp 130.

As is known, WO 92/21029 to Genentech Inc. teaches a method for determination of agonists or antagonists of growth hormones and ligands with a similar structural conformation. The potential agonists and antagonists are put into contact with a receptor for the hormone and this causes formation of a ternary complex consisting of a molecule of the potential agonist or antagonist and two molecules of such receptor for the hormone to be agonized or antagonized. Dimerization of receptors induced by a ligand molecule allows one to conclude that the ligand has two different interaction sites (site 1 and site 2), which can be mutagenized to generate agonists or antagonists.

It has now been surprisingly found that the ligands in the group of cytokines similar to Interleukin 6 (IL-6), that is Oncostatin M (OSM), Leukemia Inhibitory Factor (LIF), Ciliary Neurotrophic Factor (CNTF), and Interleukin 11 (IL-11), induce the formation of a receptor complex of which the membrane molecule gp 130 is a part. In this receptor complex the specific receptor for each of these cytokins and the membrane molecule gp 130 are always present as common elements. It is thus possible to formulate the hypothesis that site 1 and site 2 bind to two different molecules in this class of hormones: site 1 to the specific receptor and site 2 to gp 130.

Identification of the two sites is made possible, as will be seen more clearly from the following, by construction of a three-dimensional model of the receptor complex based on the functional similarity between sequences of the human growth hormone receptor (hGH) and sequences of the receptors for the hormones in question. Isolation of variants that, with respect to the wild type hormone, have a greater affinity for the specific receptor (superagonists or superantagonists) is obtained by construction of filamentous phage libraries, for example M13, carrying the hormone, both in the wild type and mutant version.

The difference between the three-dimensional model, for example of IL-6, adopted here and the one adopted in WO92/21029 leads to hypothesize different residues in helix A and C as constituents of site 2.

Modelling of the human interleukin 6 molecule is performed as follows. Knowing, from data available in scientific literature, that human interleukin 6 belongs to a class of cytokines that have four helices forming the core of their three-dimensional structure, the amino acidic sequence of human interleukin 6 was analyzed to identify the four regions in which there was the highest probability of a helix formation. In a following stage, these four helix regions of the interleukin 6 molecule were modelled in a computerized interactive graphic unit. To start, it was assumed that the orientation of the four helices might be similar to that seen in hormones such as the growth hormone or the macrophage granulocyte colony stimulation factor. To optimize packaging of the hydrophobic amino acids in the space between the four helices, adjustments to the relative positions of the helices were made. Subsequently, the loops connecting the four helices were modelled.

This three-dimensional model of interleukin 6 has enabled the identification of the two sites of interaction between human interleukin 6 and its two receptors: the low affinity receptor gp 80 (site 1) and the high affinity receptor for gp 130 signal transduction (site 2). The following procedure was used to identify the two sites. From comparison of sequences it is known that all the members of one family of hematopoietic receptors are related to each other by the fact that they share a domain, known as the cytokine recognition domain. This similarity of sequences also indicates a high probability of structural similarity in corresponding parts of the various receptors, including the two interleukin 6 receptors, gp 80 and gp 130. The observation that the cytokines that bind to these receptors all have (or can be predicted to have) a similar structure, that is a four helix matrix, strongly supports the hypothesis that the interaction between these cytokines and their receptors, by means of the cytokine recognition domain, must be very similar in biologically active complexes.

Considering that the three-dimensional structure of one of these compounds (the complex made by growth hormone and the extra-cellular domain of the dimeric receptor for the growth hormone) has been determined by means of X-ray crystallography, our model of human interleukin 6 allows us to identify the potential sites of interaction between interleukin 6 and its two receptors gp 80 (site 1) and gp 130 (site 2). This by comparison with the complex involving the growth hormone and assuming that the functionally important amino acids are located in similar positions on the surface of the two hormones.

The need to provide a methodology the production of agonists, antagonists and superantagonists for hormones of the immune system whose receptor complex includes gp 130, will be explained with reference to the case of interleukin-6.

As is known, interleukin 6 is a polypeptide of 184 amino acids which, as described, belongs to the class of helical cytokines. Interleukin 6 is a multi-functional cytokine produced by various types of cell. It acts as a differentiation and growth factor on cells of various types, such as for example cells in the immune system, hepatocytes, kidney cells, hemopoietic staminal cells, keratinocytes and neurones.

Production of superagonists of interleukin 6 would allow the use of lower therapeutic doses than those required with wild interleukin 6 in the treatment of numerous serious diseases. In fact, interleukin 6 has important and promising applications in the treatment of breast cancer, leukemia, and infectious diseases or diseases connected with disorders of the cells producing bone marrow.

On the other hand the production of antagonists or superantagonists of human interleukin 6 would allow inhibition of interleukin 6 in numerous diseases characterized by its excessive production, such as chronic autoimmune diseases, myeloma/plasmacytoma, post-menopausal osteoporosis and cancer cachexy.

The methodology for the selection of superagonists, antagonists or superantagonists of a hormone using the membrane molecule gp 130 to activate the mechanisms regulating cell physiology, according to the present invention, comprises the following operations:

comparing the amino acid sequences of the growth hormone with the sequences of said hormone;

comparing the amino acid sequences of the growth hormone receptor with those of the two receptors of the hormone in question, that is with the hormone-specific receptor and gp 130;

on the basis of the above comparisons, formulating a three-dimensional model of the receptor complex based on the functional similarity between sequences of the growth hormone receptor and the two hormone receptors in question; and identifying the residues of the wild type hormone in question that are a part of the site of interaction with the specific receptor and of the site of interaction with gp 130, respectively.

The hormone in question can be chosen from the group comprising Interleukin 6 (IL-6), Oncostatin M (OSM), Leukemia Inhibitory Factor (LIF), Ciliary Neurotrophic Factor (CNTF) and Interleukin 11 (IL-11).

For selection of superagonists of interleukin 6, the methodology according to the present invention further comprises the following additional operations:

production of a series of phage libraries containing mutations of the following wild type residues of interleukin 6, present in the form of fusion product with filamentous phage proteins Glu 42, Glu 51, Ser 52, Ser 53, Lys 54, Glu 55, Asn 63, Lys 66, Met 67, Ala 68, Glu 69, Lys 70, Asp 71, Phe 170, Gln 175, Ser 176, Ser 177, Leu 181, Gln 183;

generation of a phage library, each phage having a mutant interleukin 6 sequence;

selection, from the mixed population of phages expressing interleukin 6 mutants, of that or those with an affinity for the specific receptor greater than that of wild type interleukin; and identification of the best amino acid sequence or sequences binding the receptor by sequencing of the DNA extracted from the selected phage particles.

In this case, a series of phage libraries can be produced containing mutations of said wild residues of interleukin 6 present as a product of fusion with the protein pIII of M13.

The methodology for selecting antagonists of interleukin 6 according to the present invention comprises—along with the operations indicated above—the following operations:

mutation of the residues that to form part of the site of interaction with gp 130 (Arg 30, Tyr 31, Gly 35, Ser 37, Ala 38, Ser 118, Lys 120, Val 121, Gln 124, Phe 125, Gln 127, Lys 128 and Lys 129), using conventional molecular biology techniques;

evaluation of biological activity and affinity for the specific interleukin 6 receptor of the mutants produced as above, in order to identify variants of interleukin 6 whose affinity to the specific receptor is intact and that show reduction or loss of the biological activity; and evaluation of the above variants of interleukin 6 as antagonists for the biological activity of wild interleukin 6.

In case of selection of superantagonists of interleukin 6 by combination of the variations of amino acid sequences responsible for antagonist activity, indicated above, with amino-acid variations responsible for an increased affinity of the specific receptor for interleukin 6.

In the methodology for selecting antagonists or superantagonists of interleukin 6, the mutagenesis of the residues identified as above can be performed using a molecular biology technique chosen from the group comprising Polymerase Chain Reaction, Primer Extension, oligonucleotide Directed Mutagenesis, and combinations thereof.

The present invention is not limited to the methodology for selection of agonists, antagonists or superantagonists of interleukin 6, on the contrary, it extends to the agonists, antagonists and superantagonists of hormones using the membrane molecule gp 130 to activate mechanisms regulating cell physiology, and that can be obtained using the selection methodology described above.

Up to this point a general description of the subject of the present invention has been given. With the aid of the following examples a detailed description of specific embodiments of the invention will now be given, with the purpose of giving a better understanding of the objects, characteristics, advantages and methods of application thereof.

DEPOSITS

Figure 1:
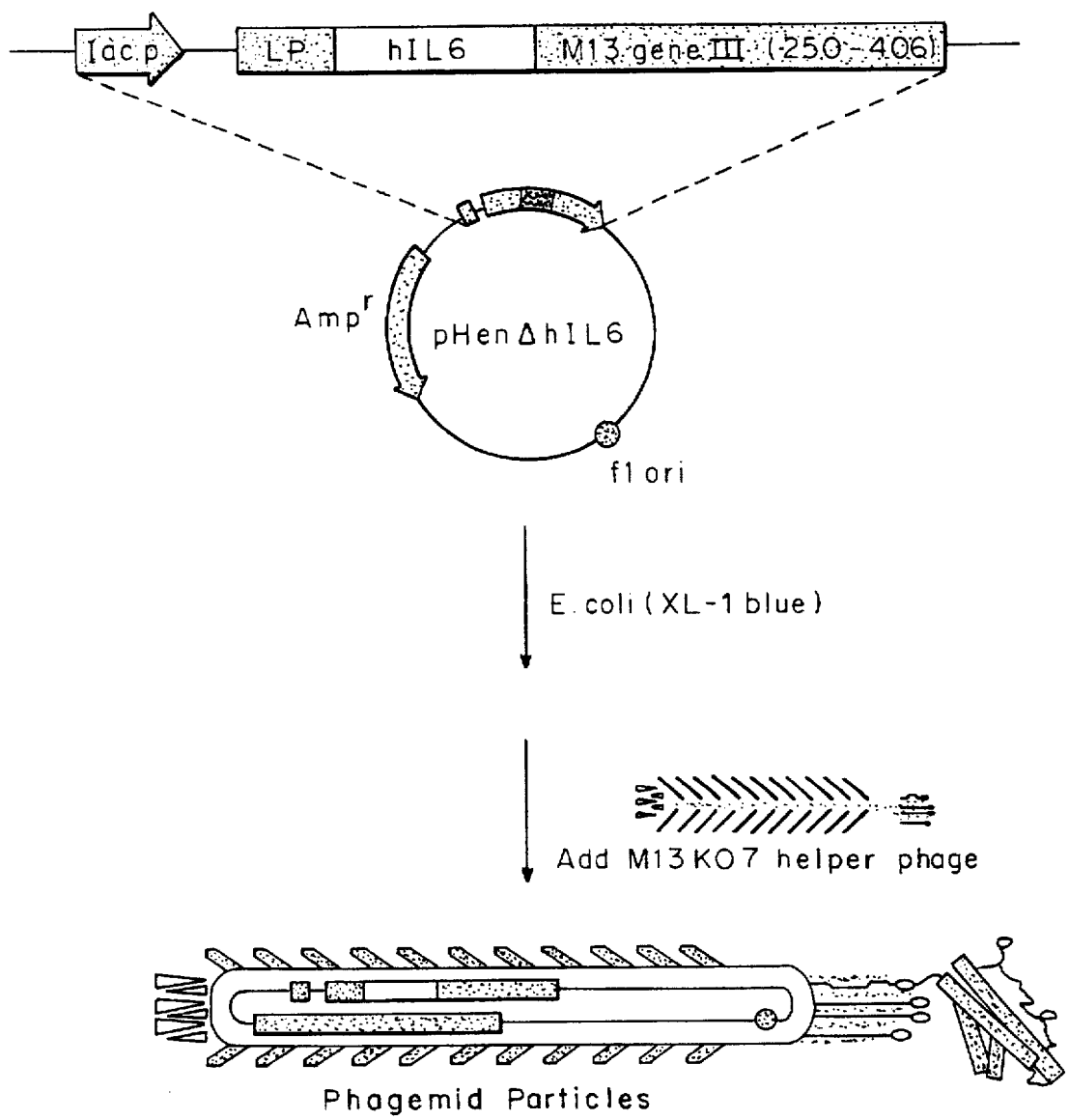
FIG. 1 shows the construct pHenΔhIL-6 and the production of phasmidic particles (see example 1, "Vector Construction"), used for selection of agonists of hIL-6.
Figure 2:
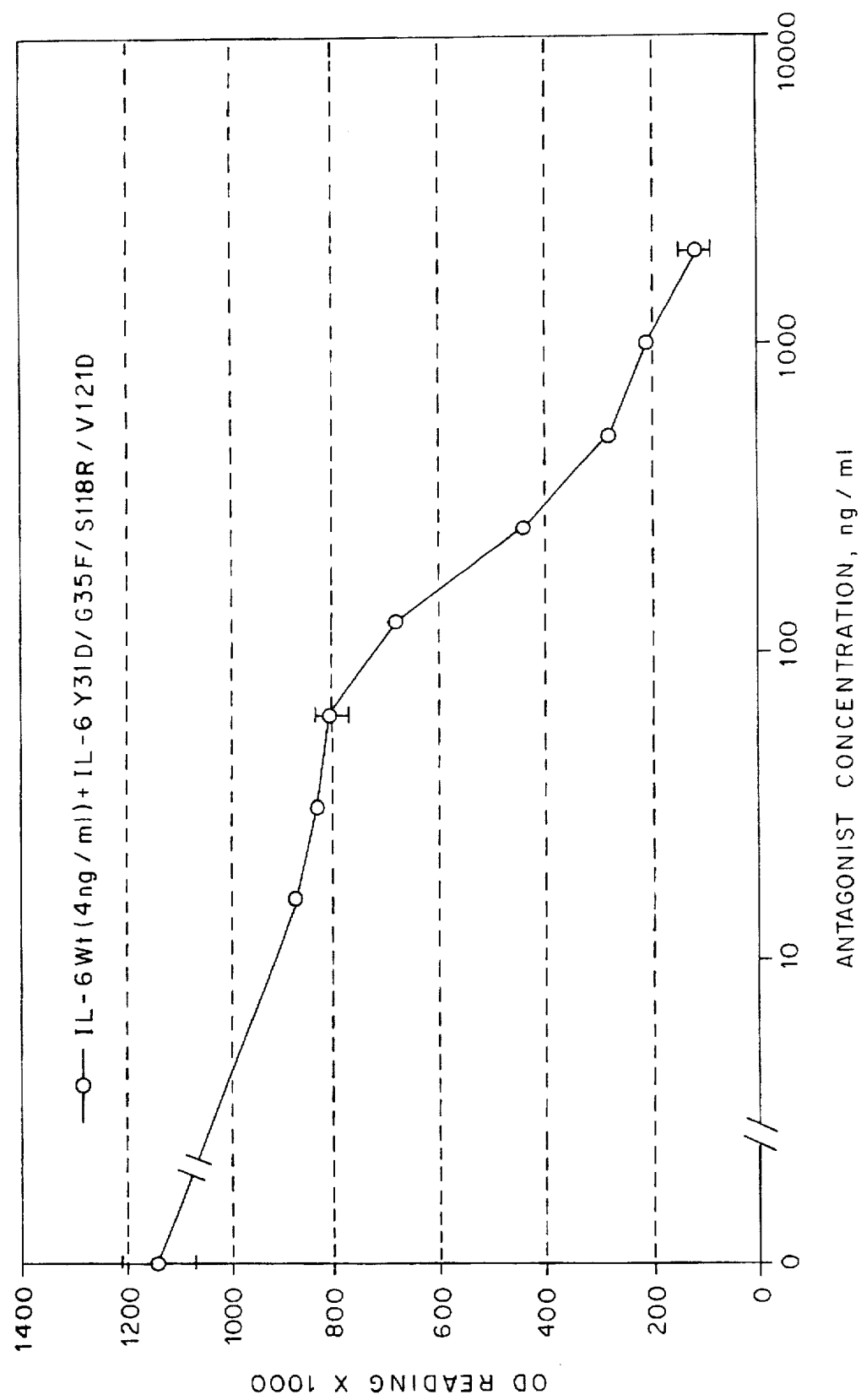
FIG. 2 shows the antagonistic activity of mutant IL-6 Tyr31Asp/Gly35Phe/Ser118Arg/Val121Asp with the increase of its concentration.

E.Coli K12 bacteria—transformed using the plasmid pHenΔhIL-6 containing, from the site for recognition of the restriction enzyme SalI to that for the restriction enzyme NotI, a nuleotidic sequence coding for the amino acid sequence of wild type human interleukin-6—have been deposited on Oct. 6, 1993 with The National Collection of Industrial and Marine Bacteria Ltd. (NCIMB), Aberdeen, Scotland, UK, with access number NCIMB 40563.

EXAMPLE 1

Application of the Methodology According to the Present Invention for the Selection of Agonists of Interleukin-6

1) VECTOR CONSTRUCTION

The strategy consists in construction of a hybrid gene containing all the region coding for hIL-6 followed by the last 157 amino acids of protein pIII of the phage M13 and preceded by the sequence Pel B, which vectors the synthesized protein to the periplasmic space.

Expression of the hybrid gene is driven by the promotor lacZ. The construction is made in the context of vector pHenΔe, and takes the name of pHenΔhIL-6 (see the only figure enclosed). This plasmid also contains a phage replication origin. If a bacterial cell containing this plasmid is infected by a bacteriophage known as a "helper", such as M13K07, single filament copies will be produced by the plasmid, and will be coated with the phage proteins, just like a true phage genome. These phage particles containing the plasmid are known as phasmids. Along with the normal pIII molecules, they also contain hIL6-pIII fusion molecules. A hIL-6 molecule and the gene coding its amino acid sequence are thus contained within the same unit. In the case of mutant molecules, it will be possible to determine the amino acid sequence of the molecules exposed on the surfaces of the phages obtained from selection processes, simply by sequencing the phasmid DNA.

A further characteristic of the construction pHen hIL-6 is the presence of a translation codon stop between the IL-6 gene and the pIII gene. Production of the hybrid protein is carried out in bacterial strains capable of suppressing this Stop codon. Vice versa the use of non-suppressor strains allows production of hIL-6 alone, directly in the periplasmic space.

The following experiments demonstrate the ability to use shrIL-6R to purify, from among the vast range of mutant interleukin-6 exposed on the phage using pHen hIL-6, those having the greatest affinity with said receptor, by means of amplification selection cycles.

2) SYSTEM CHARACTERIZATION EXPERIMENTS a) ELISA Test

The wells in ELISA plates were coated with hIL-6 phasmids or with M13K07 and made to react with shrIL-6R (soluble Human Recombinant IL-6R). After repeated washing the presence of the receptor was indicated using a specific monoclonal antibody conjugated with alkaline phosphatase. The signal obtained is greater in the case of hIL-6 phasmids and increases as the amount of receptor used increases.

b) Enrichment of the hIL-6 phasmid with phasmid-K07 mixtures using shrIL-6R hIL-6 phasmid particles were mixed with particles of M13K07 at a ratio of 1:100. This mixture was incubated with polystyrene balls coated with shrIL-6R. After repeated washing at a neutral pH the balls underwent stringent washing at pH 4.2, followed by elution at pH 3.6. The proportion of hIL-6 phasmids:M13K07 in the resulting eluant was then determined. The proportion is found to be 1:10, with a consequent enrichment by ten times of the hIL-6 phasmids with respect to M13K07.

c) Selection from mixtures of mutant interleukin-6 of those having the highest affinity for the receptor gp 80

Phasmid particles were produced having on their surface mutant molecules of hIL-6 with a higher (176 Arg) or lower (179 Ala) affinity with the receptor, compared with the natural version. These particles were mixed in a ratio of 1:1. The mixture was incubated with the receptor in a solid phase (as described in point b). In the eluate at pH 3.6, the ratio between the two types of particle was found to be 15:1 in favor of 176 Arg.

d) Determination of the relative affinity of M13K07, hIL-6 phasmid, 176 Arg phasmid and 179 Ala phasmid particles for the receptor gp 80

Equal amounts of particles of the various types listed above were incubated separately with the balls coated with receptor. After the usual washing sequence the number of particles recovered in the eluant at 3.6 was determined for each type of phage. Considering the value of particles recovered for the phasmid hIL-6 as 1, a value of 3 is obtained for 176 Arg, 0.2 for 179 Ala and 0.18 for M13K07. These values reflect the relative affinities of the molecules of IL-6 non exposed on the phage. It is, in fact, known that 176 Arg binds the receptor with an affinity three times greater than that of the natural molecule, whereas in the case of 179 Ala the affinity for the receptor is reduced almost to zero (in fact a phasmid with this mutant, as regards binding to the receptor, behaves like M13K07)

This group of experiments has shown that it is possible, using the method according to the present invention, to select from mixtures of mutants exposed on phage those having the greatest affinity for the receptor.

EXAMPLE 2

Generation and Selection of Antagonists of Interleukin 6 Using the Methodology According to the Present Invention The plasmid PhenΔhIL-6 was used as a template for all the mutagenesis reactions. This plasmid is a derivative of the plasmid pHEN1 and contains the area coding for human IL-6 (SEQ ID NO:1) with SEQ ID:2 as corresponding amino acid sequence upstream the area coding for the carboxy-terminal portion (from codon 250 to the COOH end) of the protein pIII of the bacteriophage M13; the two coding areas are in reading frame and are separated by an Amber UAG Stop codon, which can be suppressed in bacterial strains that have the gene of the suppressor SupE integrated in their genome. The area coding for human IL-6 is also in reading frame, below the peptide PelB, a signal sequence for secretion, and the whole gene is under the control of the promotor LacZ. Finally, a single site for the restriction enzyme SacI has been introduced in the nucleotide sequence coding for the amino acids 20–21–22 of hIL-6 without changing their identity and, equally, a single site for the restriction enzyme BfrI has been introduced in the area coding for the amino acids 38–39–40 of hIL-6, likewise without changing them.

A PCR strategy (Polymerase Chain Reaction) was used to generate mutations within the codons selected in the area coding for human interleukin 6. The primer downstream is H9, a 32 nucleotide primer, corresponding to positions 426–457 (antisense filament) of hIL-6 cDNA (taking the first nucleotide of the first codon of the mature polypeptide to be 1). The primer hybridization site is downstream the recognition site for the enzyme XbaI, naturally present in the cDNA. The mutagenetic primer upstream is IL-6 31D/35 PCR, a 70 nucleotides primer, whose sequence is SEQ ID NO:3.

The primer IL-6 31D/35 PCR extends from position 55 to position 124 (sense filament) of the hIL-6 cDNA and introduces degenerations into the codons coding for the amino acid 31 (wild type tyrosine) and 35 (wild type glycine). A DNA fragment of 403 pairs of bases is amplified using PCR according to standard PCR amplification protocols. Amplification is performed in 35 cycles. Each cycle consists of incubation for 2 minutes at 94° C. for denaturation of the template, 2 minutes at 50° C. for hybridization of the oligonucleotide and 3 minutes at 72° C. for extension of the chain. The amplified fragment is digested with SacI and XbaI and purified using 2% agarose gel. The fragment generated by PCR and digested by the two enzymes is ligated into the vector pHen hIL-6 digested with the same two enzymes, purified on 0.8% agarose gel, to replace the wild type sequence.

The following Table 1 shows the biological activity, in human hepatoma cells, and binding to the receptor gp 80 for wild type interleukin-6 and mutations thereof, the mutations being indicated with an asterix.

TABLE I

Receptor binding properties and biological activity of wild type interleukin 6 and its mutants in helix A

| 27 | | | 30 | | | | | 35 | | | | 40 | | | | Biological activity | Receptor binding |
|---|---|---|---|---|---|---|---|---|---|---|---|---|---|---|---|---|---|
| a) Lys* | Gln | Ile | Arg | Tyr* | Ile | Leu | Asp | Gly* | Ile | Ser | Ala | Leu | Arg | Lys | Glu | 100% | 100% |
| b) Ala | Gln | Ile | Arg | Tyr | Ile | Leu | Asp | Gln | Thr | Ser | Ala | Leu | Arg | Lys | Glu | 80 ± 19% | 100 ± 4% |
| c) Lys | Gln | Ile | Arg | Asp | Ile | Leu | Asp | Tyr | Ile | Ser | Ala | Leu | Arg | Lys | Glu | 4.5 ± 1% | 83% |

TABLE I-continued Receptor binding properties and biological activity of wild type interleukin 6 and its mutants in helix A

| 27 | | | 30 | | | | | 35 | | | | | 40 | | | Biological activity | Receptor binding |
|---|---|---|---|---|---|---|---|---|---|---|---|---|---|---|---|---|---|
| d) Lys | Gln | Ile | Arg | Asp | Ile | Leu | Asp | Phe | Ile | Ser | Ala | Leu | Arg | Lys | Glu | 2 ± 0.5% | 80 ± 2% |
| e) Lys | Gln | Ile | Arg | Asp | Ile | Leu | Asp | Leu | Ile | Ser | Ala | Leu | Arg | Lys | Glu | 6 ± 4% | 177 ± 7% |
| f) Lys | Gln | Ile | Arg | Asp | Ile | Leu | Asp | His | Ile | Ser | Ala | Leu | Arg | Lys | Glu | 38 ± 8% | 85 ± 15% |
| g) Lys | Gln | Ile | Arg | Asp | Ile | Leu | Asp | Cys | Ile | Ser | Ala | Leu | Arg | Lys | Glu | 30 ± 1% | 82 ± 18% | a) is SEQ ID NO:9
b) is SEQ ID NO:10
c) is SEQ ID NO:11
d) is SEQ ID NO:12
e) is SEQ ID NO:13
f) is SEQ ID NO:14
g) is SEQ ID NO:15

As can be seen from the table, the mutants (Tyr31Asp, Gly35Tyr), (Tyr31Asp, Gly35Phe) and (Tyr31Asp, Gly35Leu, Glu42Ala) show lower biological activity when compared with wild type interleukin 6. In all three cases the residual activity is 2–5% that of wild type interleukin-6. The three mutants maintain their full ability to bind to the interleukin 6 receptor gp 80. In conclusion, the three mutants have a decreasing signal transduction activity in hepatoma cells. In other words, they are antagonists of wild interleukin 6. in particular, the mutant (Tyr31Asp, Gly35Phe) is a particularly effective antagonist, as it is capable of reducing the activity of wild type interleukin 6 when used at 50 fold molar excess in tests on human hepatoma cells.

EXAMPLE 3

Generation and Selection of Further Antagonists of Interleukin 6 Using the Methodology According to the Present Invention The plasmid pHENΔhIL-6, described in the preceding example, was used as a template for all the mutagen reactions. A PCR strategy (Polymerase Chain Reaction) was used to generate mutations within the codons selected for the area coding for human interleukin 6. The primer above is HP/1, a primer with 29 nucleotides, corresponding to positions 1–19 (sense filament) of hIL-6 cDNA (taking the first nucleotide of the first codon of the mature polypeptide to be 1). The primer hybridization site is upstream to the site recognizing the enzyme SacI, artificially introduced in the cDNA without changing the sequence coded by the latter, as described in example 2. The mutagenetic primer below is IL-6 118RCLF/121VD, a primer with 72 nucleotides, whose sequence is SEQ ID NO 4.

The primer IL-6 118RCLF/121VD extends from position 334 to position 405 (antisense filament) of the cDNA of hIL-6 and introduces degenerations into the codons coding for the amino acid 118 (wild type serine) and 121 (wild type valine). A DNA fragment of 415 pairs of bases is amplified using PCR according to standard PCR amplification protocols. Amplification is performed in 35 cycles. Each cycle consists of incubation for 2 minutes at 94° C. for denaturation of the template, 2 minutes at 50° C. for hybridization of the oligonucleotide and 3 minutes at 72° C. for extension of the chain. The amplified fragment is digested with SacI and XbaI and purified using 2% agarose gel. The fragment generated by PCR and digested by the two enzymes is ligated into the vector pHenΔhIL-6 digested with the same two enzymes, purified on 0.8% agarose gel, to replace the wild type sequence.

The following Table 2 shows the biological activity, in human hepatoma cells, and binding to the receptor for wild interleukin-6 and versions thereof with mutations in the residues indicated.

TABLE 2

Receptor binding properties and biological activity of wild-type interleukin 6 and helix C mutations thereof

| 118 | 121 | Biological activity | Receptor binding |
|---|---|---|---|
| Ser | Val | 100% | 100% |
| Arg | Val | 66% | 81% |
| Leu | Asp | 36 ± 4% | 92% |
| Arg | Asp | 3.5 ± 0.5% | 66 ± 5% |
| Ser | Asp | 58 ± 23% | 78 ± 2% |

It can be seen that the mutant IL-6 Ser118Arg/Val121Asp has characteristics very similar to those of the mutant IL-6 Tyr31Asp/Gly35Phe, described in Table 1, that is to say it binds normally to the type I receptor of interleukin 6, but cytokin biological activity is reduced approximately thirty-fold.

EXAMPLE 4

Generation and Selection of More Powerful Antagonists of Interleukin 6 Using the Methodology According to the Present Invention In this case, the plasmid pHENΔhIL-6 Tyr31Asp/Gly35Phe, obtained as described in Example 2, was used as a template for all the mutagenic reactions.

A PCR strategy (Polymerase Chain Reaction) was used to generate mutations within the codons selected for the area coding for human interleukin 6. The primer above is HP/1, described in the previous example. The mutagenetic primer below is IL-6 118RCLF/121VD, also described in the previous example. A DNA fragment of 415 pairs of bases is amplified using PCR according to standard PCR amplification protocols. Amplification is performed in 35 cycles. Each cycle consists of incubation for 2 minutes at 94° C. for denaturation of the template, 2 minutes at 50° C. for hybridization of the oligonucleotide and 3 minutes at 72° C. for extension of the chain. The amplified fragment is digested with SacI and XbaI and purified using 2% agarose gel. The fragment generated by PCR and digested by the two enzymes is ligated into the vector pHen hIL-6 digested with the same two enzymes, purified on 0.8% agarose gel, to replace the wild type sequence.

The following Table 3 shows the biological activity, in human hepatoma cells, and binding to the receptor for wild interleukin-6 and versions thereof with mutations in the residues indicated.

TABLE 3

Receptor binding properties and biological activity of wild interleukin 6 and helix A and C mutants thereof

| Helix A | | Helix C | | Biological | Receptor |
|---|---|---|---|---|---|
| 31 | 35 | 118 | 121 | activity | binding |
| Tyr | Gly | Ser | Val | 100% | 100% |
| Asp | Phe | Leu | Val | 1.4% | N.D. |
| Asp | Phe | Arg | Val | 5.4 ± 1.1% | 66 ± 2% |
| Asp | Phe | Leu | Asp | 0% | 63 ± 4% |
| Asp | Phe | Arg | Asp | 0% | 97 ± 15% |
| Asp | Phe | Phe | Asp | 0% | 76 ± 26% |

N.D. = Not determined

Three of the variants containing mutations both on helix A and on helix C show no sign of biological activity in human hepatoma cells, whereas they maintain their ability to bind the receptor gp80. Among these three proteins, the mutant IL-6 Tyr31Asp/Gly35Phe/Ser118Arg/Val121Asp was chosen for competition experiments with wild type interleukin 6 biological activity in human hepatoma cells. The cells were stimulated with wild interleukin 6 at 4 nanograms per milliliter (ng/ml) of culture medium, in the presence of increasing concentrations of mutant. As illustrated in FIG. 2 (in which biological activity of wild type interleukin 6 is expressed in arbitrary units), increasing concentrations of the mutant manage to fully antagonize the effects of wild interleukin 6 on human hepatoma cells.

Table 4 shows the levels of inhibition (in percentage) of the biological activity of wild interleukin 6 according to the concentration of antagonist (expressed in nanograms per milliliter, molar excess compared with wild type interleukin 6 and nanomoles per liter, respectively).

TABLE 4

| Inhibition of the biological activity of wild interleukin 6 according to the concentration of antagonist | | | |
|---|---|---|---|
| IL-6 | Tyr31Asp/Gly35Phe/Ser118Arg/Val121Asp | | Inhibition of wild |
| g/ml | molar excess | concentration (nM) | IL-6 (%) |
| 16 | 4 X | 0.7 nM | 23% |
| 60 | 15 X | 2.7 nM | 28% |
| 164 | 41 X | 7.5 nM | 50% |
| 500 | 125 X | 22.7 nM | 75% |
| 1000 | 250 X | 45.5 nM | 82% |
| 2000 | 500 X | 90.0 nM | 90% |
| 4000 | 1000 X | 181.8 nM | 96% |

EXAMPLE 5

The Interleukin 6 Antagonist, Generated and Selected Using the Methodology Described in the Present Invention, Inhibit Interleukin 6-Dependent Growth of Human Myeloma Cells In the previous example it was shown that one of the mutants, namely IL-6 Tyr31Asp/Gly35Phe/Ser118Arg/Val121Asp was able to inhibit interleukin 6 biological activity (stimulation of transcription by an interleukin 6 inducible promoter) on human hepatoma cells. In the introductory part of this patent application it is stated that development of interleukin 6 antagonists or superantagonists would have practical application because they could be used to inhibit interleukin 6 activity in diseases characterized by interleukin 6 overproduction, like various forms of multiple myeloma/plasmacytoma. We provide here a further example by showing that the three mutants IL-6 Tyr31Asp/Gly35Phe/Ser118Arg/Val121Asp (DFRD), IL-6 Tyr31Asp/Gly35Phe/Ser118Phe/Val121Asp (DFFD), IL-6 Tyr31Asp/Gly35Phe/Ser118Leu/Val121Asp (DFLD)

fully inhibit the interleukin 6-dependent growth of a human myeloma cell line, called XG-1, derived from freshly isolated myeloma cells from a patient with terminal disease. The XG-1 myeloma cell line growth is strictly dependent on exogenously added interleukin 6, similarly to what has been shown for fresh myeloma cells, therefore this cell line can be considered an excellent in vitro model of the multiple myeloma disease (Jourdan, M., Zhang, X-G., Portier, M., Boiron, J. -M., Bataille, R. and Klein, B.(1991) J. Immunol. 147, 4402–4407). To test mutants antagonism on wild type interleukin 6, XG-1 myeloma cells were cultured in 96-well microtiter plates at 6000 cell/microwell with wild type interleukin 6 at 0.1 nanograms per milliliter (ng/ml) of culture medium, in the presence of increasing concentrations of each one of the three mutants. After 7 days of culture, cell numbers were evaluated by calorimetric determination of hexosaminidase levels (Landegren, U. (1984) J. Immunol. Methods 67, 379–388). The following Table 5 shows the inhibition of wild type interleukin 6 activity as a function of the three antagonist concentrations (expressed in nanograms of mutant per milliliter of colture medium).

TABLE 5

Inhibition of wild type interleukin 6 activity (stimulation of growth of XG-1 human myeloma cells) as a function of the three antagonists concentration.

| | Inhibition of wild type interleukin 6 produced by concentration | | |
|---|---|---|---|
| Antagonist | DFRD | DFFD | DFLD |
| 3.3 ng/ml | 6% | 0% | 0% |
| 10 ng/ml | 12% | 7% | 3% |
| 30 ng/ml | 25% | 18% | 10% |
| 90 ng/ml | 42% | 35% | 31% |
| 270 ng/ml | 64% | 59% | 53% |
| 810 ng/ml | 84% | 84% | 71% |
| 2430 ng/ml | 90% | 90% | 76% |
| 7290 ng/ml | 93% | 95% | 81% |

As can be seen from the table, all mutants are particularly effective antagonists of interleukin 6 biological activity on human myeloma cells.

EXAMPLE 6

Application of the Methodology According to the Present Invention for the Selection of Novel Superagonists of Interleukin 6

A phage library (containing mutations of residues Gln 175, Ser 177, Leu 181 and Leu 183 of wild type interleukin 6, present in the form of fusion product with filamentous phage protein) was constructed using the Primer Extension molecular biology technique. The mutagenetic oligonucleotide is IL-6 QSLQ (AS), a 62 nucleotides oligo, whose sequence is SEQ ID NO:5. Primer IL-6 QSLQ (AS) extends from position 507 to the stop codon of the interleukin 6 cDNA (antisense strand), it introduces degenerations into codons coding for the amino acids 175 (wild type Gln), 177 (wild type Ser), 181 (wild type Leu) and 183 (wild type Gln) and it also introduces a NotI restriction site downstream of the interleukin 6 stop codon. Oligonucleotide IL-6 QSLQ pr. Bam, whose sequence is SEQ ID NO:6, was used as primer for the Primer Extension reaction. oligonucleotide IL-6 QSLQ pr. Bam extends from position 503 to position 522 (sense strand) of the interleukin 6 cDNA and it contains a BamHI recognition site within the 5' nine nucleotides. The two oligonucleotides are complementary to each other on a region corresponding to position 507 through position 522 of the interleukin 6 cDNA. The two oligonucleotides were annealed in vitro, and the annealed oligonucleotides were used as substrate for a Primer Extension reaction, performed using the Klenow enzyme. The double-stranded DNA fragment thus obtained was then digested with BamHI (compatible with BglII) and with NotI and ligated into the plasmid phenΔhIL-6, digested with BglII (compatible with BamHI) and with NotI, in order to replace the wild type sequence with the mutated ones. The ligation product was inserted in bacteria, yielding roughly one million independent transformants ("trasformant" is the definition given to a bacterium which has incorporated a recombinant plasmid). The transformed bacteria were infected by with the M13K07 helper bacteriophage to generate the phage library (a library of phasmids) as described in the example 1.

The library underwent selection by incubation with polystyrene balls coated with shrIL-6R, as described in the example 1. The phage population eluted at pH 3.6 was then amplified in bacteria. After five cycles of selection-amplification, randomly selected phages were sequenced over the mutagenized region, the corresponding mutant interleukin 6 proteins were produced in the periplasmic space of the appropriate bacterial strain (as described in the example 1) and tested for both receptor binding and biological activity on human hepatoma cells. Table 6 below shows that, by using the methodology to the present invention, it is possible to select superagonists of interleukin 6, mutant molecules which have increased both receptor binding and biological activity on human hepatoma cells.

TABLE 6

Receptor binding properties and biological activities of wild type intyerleukin 6 and of its mutants in the helix D

| Position | 175 | 177 | 181 | 183 | Receptor binding (%) | Biological activity (%) |
|---|---|---|---|---|---|---|
| wild type | Gln | Ser | Leu | Gln | 100% | 100% |
| phage 5-4 | Gln | Ser | Leu | Tyr | 240% | 130% |
| phage 5-8 | Gln | Ser | Leu | Ala | 240% | 120% |
| phage 5-2 | Ile | Ser | Leu | Ala | 260% | 150% |
| phage 4-8 | Gln | Ser | Ile | Asn | 100% | N. D. |
| phage 5-3 | Ile | Ser | Val | His | 80% | N. D. |

N. D.: not determined

The mutations selected by the methodology according to the present invention can be used as starting point for the development of more potent interleukin 6 superagonists. This is shown in this example, in which the mutation identified in the phage 5-2 are combined with the mutation Ser176Arg, which by prior art is known to increase both receptor binding and biological activity (see International Publication WO 94/11402 of a PCT application of the present Applicant, filed 2.11.93 with Italian priority of 6.11.92). The three mutations were grouped on the same cDNA by mean of Oligonucleotide Directed Mutagenesis. Oligonucleotide 175I/176R/183A (S), whose sequence is SEQ ID NO:7 is 73 nucleotides long which extends from position 499 to the stop codon (sense strand) of the interleukin 6 CDNA present in phen hIL-6 and which has a recognition site for the enzyme NotI downstream of the stop codon. Oligonucleotide 175I/176R/183A (AS), whose sequence is SEQ ID NO:8, is 73 nucleotides long which extends from position 499 to the stop codon (antisense strand) of the interleukin 6 cDNA present in phenΔhIL-6 and which has a recognition site for the enzyme NotI upstream of the stop codon. The two oligonucleotide are complementary to each other and they both encode the amino acid Isoleucine in position 175, the amino acid Serine in position 176 and the amino acid Alanine in position 183. The two oligonucleotides were annealed in vitro, the double-stranded DNA fragment thus obtained was digested with the restriction enzymes BglII and Not I and ligated into the vector phenΔhIL-6 digested with the same two enzymes, in order to replace the wild type sequence with the mutated one. The corresponding interleukin 6 variant carrying the three desired mutations was produced in the periplasmic space of the appropriate bacterial strain (as described in the example 1) and tested for both receptor binding and biological activity on human hepatoma cells. The following Table 7 shows the receptor binding properties and the biological activity on human hepatoma cells of both the new triple mutant and of the parental double mutant.

TABLE 7

Receptor binding properties and biological activities of wild type intyerleukin 6 and of both double and triple mutants in helix D

| Position | 175 | 176 | 183 | Receptor binding (%) | Biological activity (%) |
|---|---|---|---|---|---|
| wild type | Gln | Ser | Gln | 100% | 100% |
| phage 5-2 | Ile | Ser | Ala | 260% | 150% |
| triple mutant | Ile | Arg | Ala | 450% | 260% |

As can be seen from the table, the mutant carrying the substitutions Gln175Ile/Ser176Arg/Gln183Ala is a much more effective interleukin 6 superagonist than the parental mutant carrying only the two substitutions Gln175Ile/Gln183Ala.

EXAMPLE 7

Application of the Methodology According to the Present Invention for the Selection of Superantagonists of Interleukin 6

The three mutations Gln175Ile/Ser176Arg/Gln183Ala, identified in the example 6, which strongly increases the receptor binding capacity, were combined with the four mutations Tyr31Asp/Gly35Phe/Ser118Arg/Val121Asp, described in examples 4 and 5, which show the strongest antagonistic behaviour, by mean of a PCR strategy. The corresponding mutant protein, called SAnt 1 and containing all the seven mutations, was tested both for receptor binding and for antagonistic behaviour on human hepatoma and myeloma cells. The following table 8 shows the receptor binding properties of both SAnt 1 and DFRD (the mutant from which SAnt 1 was derived), together with the amounts (in nanograms of mutant per milliliter of colture medium) of mutant necessary to inhibit 50% of interleukin 6 biological activity (hepatoma cells were stimulated with 4 nanograms of wild type interleukin 6 per milliliter of colture medium, while myeloma cells were stimulated with 0.1 nanograms of interleukin 6 per milliliter of colture medium, due to the higher sensitivity of the latter cells to wild type interleukin 6).

TABLE 8

Inhibition of wild type interleukin 6 activity on both human hepatoma and myeloma cells as a function of the antagonists receptor binding capacity.

| Antagonist | Receptor binding (% of wt) | 50% inhibition of interleukin 6 activity or | |
|---|---|---|---|
| | | hepatoma cells | myeloma cells |
| | | Hep3B | HepG2 | XG-1 |
| DFRD | 97% | 164 ng/ml | 132 ng/ml | 190 ng/ml |

TABLE 8-continued

Inhibition of wild type interleukin 6 activity on both human hepatoma and myeloma cells as a function of the antagonists receptor binding capacity.

| Antagonist | Receptor binding (% of wt) | 50% inhibition of interleukin 6 activity or | |
|---|---|---|---|
| | | hepatoma cells | myeloma cells |
| | | Hep3B | HepG2 | XG-1 |
| SAnt1 | 406% | 19 ng/ml | 32 ng/ml | 22 ng/ml |

As can be seen from the table, the introduction of the three mutations described in the example 6 (Gln175Ile/Ser176Arg/Gln183Ala) has at once increased the receptor binding capacity of the parental mutant DFRD and strongly decreased the amount of antagonist needed to inhibit 50% of interleukin 6 biological activity on all cell lines tested, therefore generating a very effective interleukin 6 superantagonist.

We claim:

1. An interleukin 6 receptor antagonist, wherein residue Tyr31 of human interleukin 6 is replaced with Asp and residue Gly35 of human interleukin 6 is replaced with Tyr, Phe or Leu.

2. The interleukin 6 receptor antagonist according to claim 1, wherein residue Ser118 of human interleukin 6 is replaced with Arg, Phe or Leu and residue Val121 of human interleukin 6 is replaced with Asp.

3. The interleukin 6 receptor antagonist according to claim 2, wherein human interleukin 6 residue Tyr31 is replaced with Asp, Gly35 is replaced with Phe, Ser118 is replaced with Arg, and Val121 is replaced with Asp.

4. The interleukin 6 receptor antagonist according to claim 3, wherein human interleukin 6 residue Tyr31 is replaced with Asp, Gly35 is replaced with Phe, Ser118 is replaced with Arg, Val121 is replaced with Asp, Gln175 is replaced with Ile, Ser176 is replaced with Arg, and Gln183 is replaced with Ala.

5. The interleukin 6 receptor antagonist according to claim 2, wherein human interleukin 6 residue Tyr31 is replaced with Asp, Gly35 is replaced with Phe, Ser118 is replaced with Phe, and Val121 is replaced with Asp.

6. The interleukin 6 receptor antagonist according to claim 2, wherein human interleukin 6 residue Tyr31 is replaced within Asp, Gly35 is replaced with Phe, Ser118 is replaced with Leu, and Val121 is replaced with Asp.

* * * * *